(12) United States Patent
Stauffer

(10) Patent No.: US 7,696,390 B2
(45) Date of Patent: Apr. 13, 2010

(54) METHANOL SYNTHESIS

(76) Inventor: John E. Stauffer, 6 Pecksland Rd., Greenwich, CT (US) 06830

( * ) Notice: Subject to any disclaimer, the term of this patent is extended or adjusted under 35 U.S.C. 154(b) by 0 days.

(21) Appl. No.: 12/136,142

(22) Filed: Jun. 10, 2008

(65) Prior Publication Data

US 2009/0306437 A1  Dec. 10, 2009

(51) Int. Cl.
*C07C 29/14* (2006.01)
(52) U.S. Cl. ...................................... 568/893
(58) Field of Classification Search .................. 568/893
See application file for complete search history.

(56) References Cited

U.S. PATENT DOCUMENTS

| | | | |
|---|---|---|---|
| 1,849,844 A | | 3/1932 | Stewart |
| 2,276,192 A | * | 3/1942 | Hanford et al. ............. 568/862 |
| 5,070,016 A | | 12/1991 | Hallberg |
| 6,452,058 B1 | | 9/2002 | Schweizer et al. |
| 6,486,368 B1 | * | 11/2002 | Zhou et al. .................. 568/893 |
| 7,199,276 B2 | | 4/2007 | Sher et al. |
| 7,214,721 B2 | | 5/2007 | Eastland |
| 7,288,689 B2 | | 10/2007 | Janssen et al. |
| 2007/0282018 A1 | | 12/2007 | Jenkins et al. |

FOREIGN PATENT DOCUMENTS

| DE | 362746 C | 10/1922 |
|---|---|---|
| WO | 2008/080767 A1 | 10/2008 |

OTHER PUBLICATIONS

V.N. Ipatieff, G. S. Monroe: "Synthesis of Methanol from Carbon Dioxide and Hydrogen over Copper-Alumina Catalysts. Mechanism of Reaction" J. Am. Chem. Soc., vol. 67, No. 12, Dec. 1945, pp. 2168-2171, SP002543626.
International Search Report, PCT/EP2007/063570, mailed Dec. 3, 2008.
European Search Report, EP 09 25 1524, Sep. 1, 2009.

* cited by examiner

*Primary Examiner*—Sikarl A Witherspoon
(74) *Attorney, Agent, or Firm*—Young Basile Hanlon & MacFarlane, P.C.

(57) ABSTRACT

A process is disclosed for the synthesis of methanol from methane comprising three reaction steps operated in tandem. In the first step methylene chloride is produced by the reaction of methane with oxygen and hydrogen chloride. In the second step, methylene chloride is hydrolyzed to formaldehyde, which is hydrogenated in the third step to provide the product methanol.

5 Claims, 2 Drawing Sheets

METHANOL SYNTHESIS

FIELD OF THE INVENTION

The present invention relates to a process for manufacturing methanol from methane. In the process, methane is oxychlorinated with oxygen and hydrogen chloride to methylene chloride. The latter compound is hydrolyzed with water to give formaldehyde, which in turn is hydrogenated to provide the product methanol.

BACKGROUND

The only commercial process for the production of methanol starts with the generation of synthesis gas containing carbon monoxide and hydrogen. When natural gas is the raw material, synthesis gas can be formed by reacting methane with carbon dioxide and water over a catalyst. The resulting synthesis gas is converted to methanol at a high pressure using a suitable catalyst.

Numerous improvements have been made, in the methanol process since it was introduced in the 1920's. Nevertheless, this process is handicapped by high capital investment to produce the synthesis gas and by the need lo operate the conversion step at elevated pressures to overcome unfavorable equilibrium conditions.

Recognizing the drawbacks of present-day technology, industry has made several attempts to provide a more efficient process for ethanol synthesis. One of these methods is outlined in U.S. Pat. No. 6,452,058 assigned to Dow Global Technologies, Inc. In this process, methane is oxychlorinated with oxygen and hydrogen chloride to produce methyl chloride, which then is hydrolyzed with water to provide methanol and hydrogen chloride. By recycling the hydrogen chloride to the first step, a balanced operation can be achieved.

On paper, the Dow process appears to be ideal. One diff difficulty with this process, however, is the hydrolysis reaction. At equilibrium, only a limited quantity of methyl chloride is converted to methanol. A further problem with the Dow process is the formation of higher chlorinated methane compounds in the oxychlorination step.

With these results in mind, it is an object of the present invention to provide for an improved process for the manufacture of methanol from methane. A further goal is to achieve low capital investment. These objects, as well as other features and advantages of the present invention, will be apparent from the following description and the figures that are included.

SUMMARY OF THE INVENTION

A process is provided for the synthesis of methanol starting with methane. The process comprises thee separate reactions operated in tandem.

In the first reaction, methane is oxychlorinated with oxygen and hydrogen chloride to produce methylene chloride. This reaction is promoted by a catalyst.

The second reaction involves the hydrolysis of methylene chloride with water to yield formaldehyde and hydrogen chloride. Various catalysts may be employed in this reaction.

Finally, the third reaction consists of hydrogenation of formaldehyde with hydrogen to form methanol. This reaction also requires a catalyst.

By recycling hydrogen chloride from the second reaction to the first reaction, it is possible to achieve a balanced process that is independent from a source of chlorine.

Besides producing methylene chloride, the first reaction will generate methyl chloride. This intermediate is recycled so as to produce additional methylene chloride.

Inevitably some chloroform and carbon tetrachloride will also be produced in the first reaction. These byproducts may be recovered and then reduced with hydrogen to form methylene chloride and hydrogen chloride.

Other applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein.

DETAILED DESCRIPTION

The features of the present invention can best be described by the following equations:

$$CH_4 + 2\,HCl + O_2 \rightarrow CH_2Cl_2 + 2\,H_2O \quad (1)$$

where $CH_4$ is methane, $HCl$ is hydrogen chloride, $O_2$ is oxygen, $CH_2Cl_2$ is methylene chloride, and $H_2O$ is water.

$$CH_2Cl_2 + H_2O \rightarrow CH_2O + 2\,HCl \quad (2)$$

Where $CH_2O$ is formaldehyde.

$$CH_2O + H_2 \rightarrow CH_3OH \quad (3)$$

where $H_2$ is hydrogen and $CH_3OH$ is methanol or methyl alcohol.

the first reaction step, known oxychlorination, methane is most likely supplied by natural gas, which is the largest source of this reactant worldwide. This chemical reaction will first produce methyl chloride with the formula $CH_3Cl$. By returning this intermediate to the reactor, additional methylene chloride is formed.

The first reaction requires an oxychlorination catalyst, many examples of which are disclosed in the literature. Although their compositions vary widely, almost all of them incorporate a copper salt. Because methane is unreactive, the oxychlorination reaction must be carried; out at a sufficiently high temperature to obtain favorable kinetics. A reaction temperature of 450° C. is generally suitable, but an extended range from 375° C. to 500° C. may be considered.

Figure 1:
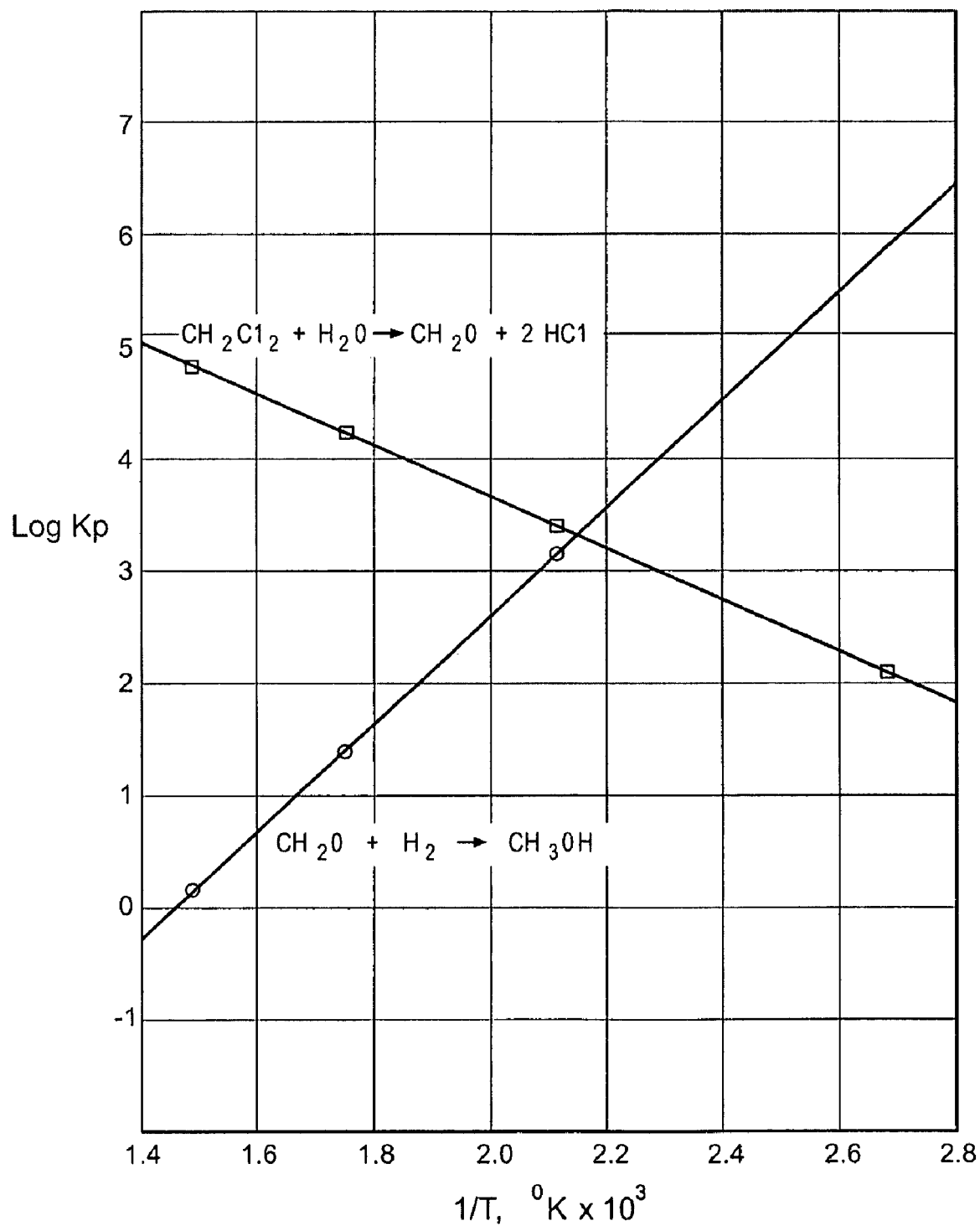
FIG. 1 is a graph showing the conversions at equilibrium for the hydrolysis of methylene chloride to formaldehyde and for the hydrogenation of formaldehyde to methanol.

The hydrolysis reaction of equation 2 has been investigated on a limited basis. Thermodynamic calculations indicate that the equilibrium is quite favorable. At 200° C. the logarithm of the equilibrium constant, $K_P$, is 3.40, and at 400° C., log. $K_p$ equals 4.83. These results are shown in FIG. 1. A catalyst can be used to achieve higher reaction rates. Methylene chloride will yield formaldehyde when it is reacted with steam over activated carbon at 260° to 270° C. Methylene chloride with steam over tin phosphate at 460° C. gives formaldehyde plus hydrogen chloride.

The production of methanol by the hydrogenation of formaldehyde as shown by equation 3 is counterintuitive. Just the reverse of this reaction is used to supply industry with enormous quantities of formaldehyde. Silver and copper gauze may be employed as dehydrogenation catalysts to promote the reaction of equation 3. Potential alternative catalysts include nickel and platinum.

The thermodynamics for the reaction of equation 3 are favorable. At 200° C., log. $K_p$ equals 3.15 and at 400° C., log. $K_p$ is 0.14. These results are shown in FIG. 1. From these data it is apparent that good yields of product can be obtained without resorting to extreme conditionals such as the elevated pressure used in existing methanol plants. As indicated by equation 3, however, there is a reduction in volume of gases during hydrogenation. Thus, the use of mild pressures, say about 10 atmospheres, may be advantageous.

In order to achieve a viable operation, the individual reaction steps, reviewed above, are preferably integrated into a unified process. Accordingly, the hydrogen chloride produced in the second reaction is recycled to the oxychlorination step. In addition, allowance must be made for chloroform and carbon tetrachloride produced in this oxychlorination reaction. The preferred approach is to recover these byproducts and then hydrogenate them to produce more methylene chloride as shown by the following equation:

$$CHCl_3 + H_2 \rightarrow CH_2Cl_2 + HCl \qquad (4)$$

where $CHCl_3$ is chloroform.

The reaction shown by equation 4 requires a catalyst. Leading contenders for this catalyst would be based on cobalt-molybdenum or nickel-molybdenum complexes, both of which have been found to be effective for hydrodesulferization. Thermodynamics for the reaction of equation 4 is extremely favorable. Therefore, it is only a matter of trial and, error to identify the optimum conditions.

Figure 2:
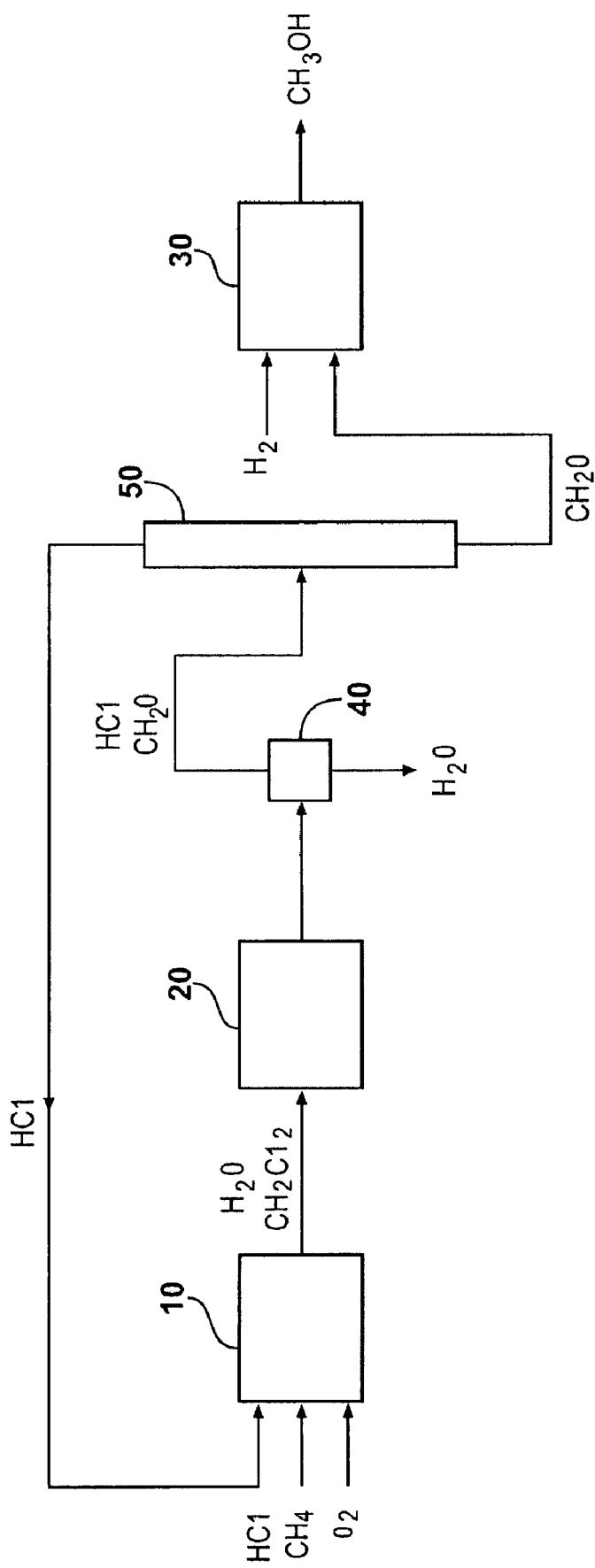
FIG. 2 is a schematic flow sheet of the process showing the principal pieces of equipment.

The process of the present invention can best be visualized by the flow sheet shown in FIG. 2. In this illustration, 10 is the oxychlorination factor, 20 is the hydrolysis reactor, and 30 is the hydrogenation reactor. A phase separator 40 is shown to remove excess water from the effluent of the hydrolysis reactor. Distillation column 50 is employed to separate byproduct hydrogen chloride, which is recycled to the oxychlorination factor. Several product streams are not shown to avoid unnecessary detail. For example, the methyl chloride and chloroform/carbon tetrachloride streams are missing from the flow sheet.

The present invention represents a completely new approach in the ongoing effort to reduce the manufacturing cost of methanol. Any success in this endeavor should be significant because of the importance of methanol in world commerce.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A process for the synthesis of methanol comprising the following steps:
   a. the reaction of methane with oxygen and hydrogen chloride to produce methylene chloride and water,
   b. the reaction of methylene chloride with water to form formaldehyde and hydrogen chloride, and
   c. the reaction of formaldehyde with hydrogen in the gas phase in the presence of a catalyst to produce methanol.

2. A process according to claim 1 in which hydrogen chloride produced in the second reaction is recycled to the first reaction.

3. A process according to claim 1 in which the chloroform and carbon tetrachloride that are produced in the first reaction are reacted with hydrogen to produce methylene chloride.

4. A process according to claim 1 wherein step a. is promoted with a catalyst.

5. A process according to claim 1 wherein step b. is promoted with a catalyst.

* * * * *